United States Patent
Chen et al.

(10) Patent No.: US 9,474,682 B2
(45) Date of Patent: Oct. 25, 2016

(54) LIGHT GUIDE TYPE PAIN RELIEVER

(71) Applicant: STAR GENERATION LIMITED TAIWAN BRANCH, Taipei (TW)

(72) Inventors: Roger Chen, New Taipei (TW); Ming-Chih Tsai, Tainan (TW)

(73) Assignee: Star Generation Limited Taiwan Branch, Taipei (TW)

( * ) Notice: Subject to any disclaimer, the term of this patent is extended or adjusted under 35 U.S.C. 154(b) by 659 days.

(21) Appl. No.: 13/864,856

(22) Filed: Apr. 17, 2013

(65) Prior Publication Data

US 2014/0065570 A1 Mar. 6, 2014

Related U.S. Application Data

(63) Continuation-in-part of application No. 13/603,649, filed on Sep. 5, 2012.

(51) Int. Cl.
  *A61H 23/02* (2006.01)
  *A61N 5/06* (2006.01)

(52) U.S. Cl.
  CPC .......... *A61H 23/0254* (2013.01); *A61H 23/02* (2013.01); *A61N 5/0601* (2013.01); *A61N 5/0603* (2013.01); *A61N 5/0613* (2013.01); *A61H 2201/0153* (2013.01); *A61N 2005/063* (2013.01); *A61N 2005/0606* (2013.01)

(58) Field of Classification Search
  CPC ............. A61H 23/02; A61H 23/0254; A61H 23/0263; A61H 7/003; A61H 7/005; A61H 2201/0153; A61C 1/081; A61C 1/088; A61N 5/0603; A61N 5/0601; A61N 5/0613
  See application file for complete search history.

(56) References Cited

U.S. PATENT DOCUMENTS

| | | | |
|---|---|---|---|
| 6,139,553 A * | 10/2000 | Dotan | A45D 34/041 601/70 |
| 6,176,824 B1 * | 1/2001 | Davis | A61B 1/24 600/178 |
| 2011/0319812 A1 * | 12/2011 | Goldberg | A61M 5/422 604/22 |
| 2012/0070799 A1 * | 3/2012 | Metcalf | A61C 1/081 433/118 |

FOREIGN PATENT DOCUMENTS

WO  WO-2010/111611 A2 * 9/2010 ............. A61H 7/005

* cited by examiner

*Primary Examiner* — Justine Yu
*Assistant Examiner* — Kathrynn Lyddane
(74) *Attorney, Agent, or Firm* — Alan D. Kamrath; Kamrath IP Lawfirm, P.A.

(57) ABSTRACT

A light guide type pain reliever includes a handle including a barrel accommodating a battery, a rear end cap and a front end cap respectively capped on two opposite ends of the barrel, a pushbutton mounted in the rear end cap and a switching connector mounted in the rear end cap and electrically connected to the battery and drivable by the pushbutton to switching on/off the battery, a holder shell connected to the front end cap and electrically coupled to the battery and having electrically connected thereto a vibrator and a light-emitting device, an adapter connected to the holder shell, and a light guide plate connected to the adapter guiding out light rays emitted by the light-emitting device.

13 Claims, 5 Drawing Sheets

LIGHT GUIDE TYPE PAIN RELIEVER

The present invention is a continuation-in-part of U.S. patent application Ser. No. 13/603,649.

BACKGROUND OF THE INVENTION

1. Field of the Invention

The present invention relates to medical implements and more particularly, to a light guide type pain reliever that provides vibration and illumination functions.

2. Description of the Related Art

Today's dental technology has been mature, unlike the rough techniques of early dental clinics. However, many people are still afraid to visit the dentist today. Even a mature-age person may feel uneasy or nervous when sitting on the consultation chair. When going to inject medicine in the patient's mouth during a dental treatment, the patient's fear may arise.

In order to reduce the patient's anxiety and fear, the most common method is to let the patient inhale a nitrous oxide and oxygen mixture before surgery, helping the patient calm down and relax. Thus, the patient's pain can be reduced when taking an injection of local anesthetics or drugs. However, not every dental clinic can afford to buy nitrous oxide and oxygen mixture supply equipment. Further, a potential crisis exists in using this kind of equipment, i.e., this kind of equipment is not suitable for use in a human streamlined clinic.

A pain reliever is known comprising a retractor and a handle. The handle has mounted therein a vibrator. The retractor can be used to drag the oral edge and to transmit vibrating waves to the oral edge, transferring the patient's attention, and thus, the patient's pain can be reduced when taking an injection of local anesthetics or drugs.

The aforesaid prior art pain reliever is convenient for use. However, the retractor can simply drag the oral edge, i.e., it is not applicable to any other area of the patient that does not allow traction. Therefore, there is a strong demand for a pain reliever that eliminates the aforesaid problem.

SUMMARY OF THE INVENTION

The present invention has been accomplished under the circumstances in view. It is one object of the present invention to provide a light guide type pain reliever, which can be pressed on the patient's affected area to guide a medication injection accurately, and which is controlled to transfer vibrating waves to the patient's affected area to reduce the patient's pain during the medication injection.

It is another object of the present invention to provide a light guide type pain reliever, which uses a light guide plate as a depressor plate, so that the light guide plate can illuminate the surroundings when it is pressed on the patient's affected area.

To achieve these and other objects of the present invention, a light guide type pain reliever comprises a hollow handle, which comprises a barrel accommodating therein a battery, a rear end cap capped on one end of the barrel, a pushbutton mounted in the rear end cap, a front end cap thread-connected to an opposite end of the barrel and a switching connector mounted in the rear end cap and electrically connected to the battery and drivable by the pushbutton to switch on/off the battery, a holder shell connected to the front end cap and electrically coupled to the battery and having electrically connected thereto a vibrator and a light-emitting device, an adapter connected to the holder shell and adapted to accommodate the vibrator and the light-emitting device and provided with a plug hole in a front side thereof, and a light guide plate having one end thereof plugged into the plug hole of the adapter and kept in line with the light-emitting device for receiving light rays emitted by the light-emitting device and having an opposite end thereof suspended outside the adapter and provided with an insertion slot.

Other advantages and features of the present invention will be fully understood by reference to the following specification in conjunction with the accompanying drawings, in which like reference signs denote like components of structure.

DETAILED DESCRIPTION OF THE PREFERRED EMBODIMENTS

Figure 1:
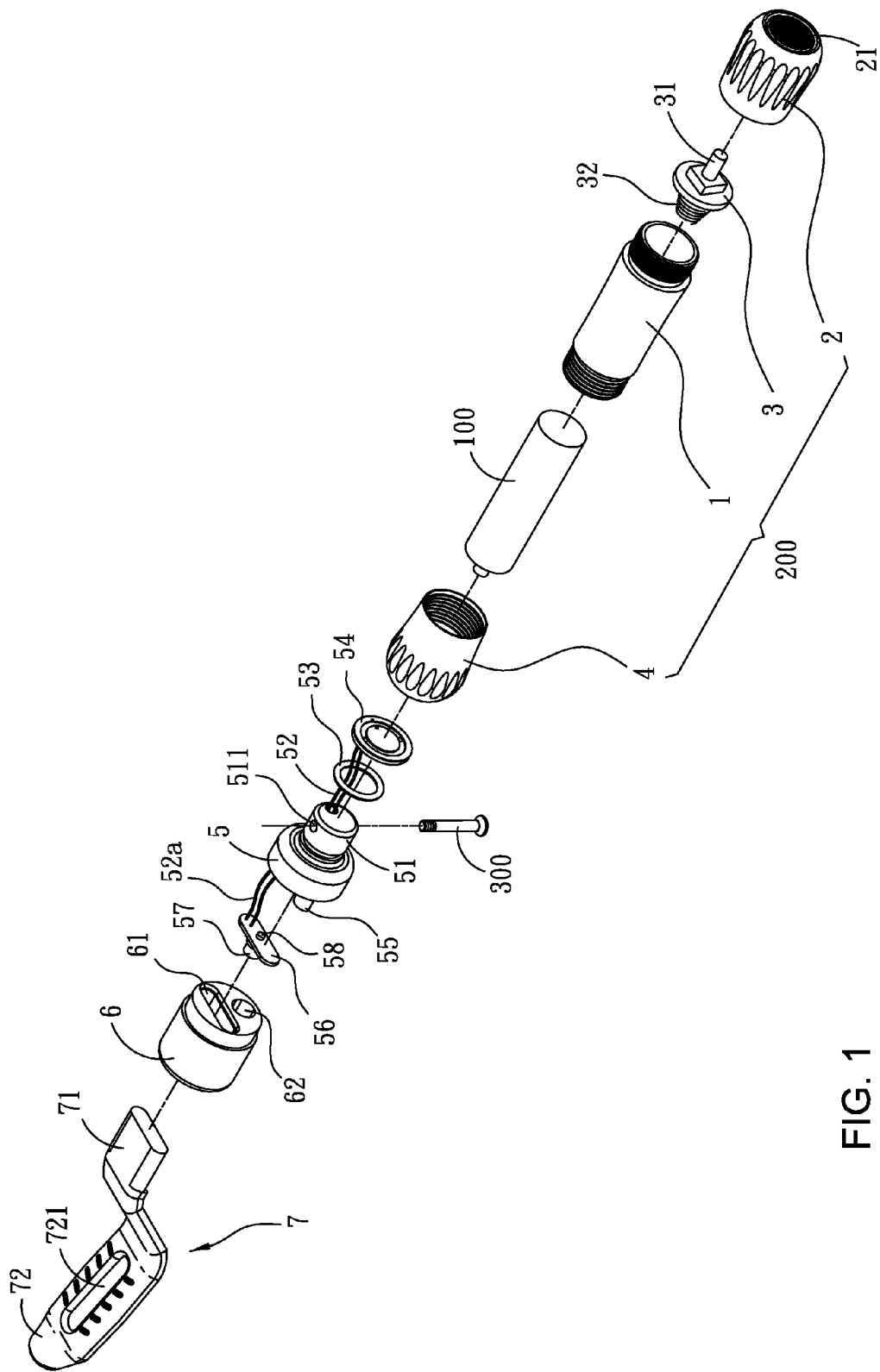
FIG. 1 is an exploded view of a light guide type pain reliever in accordance with the present invention.
Figure 2:
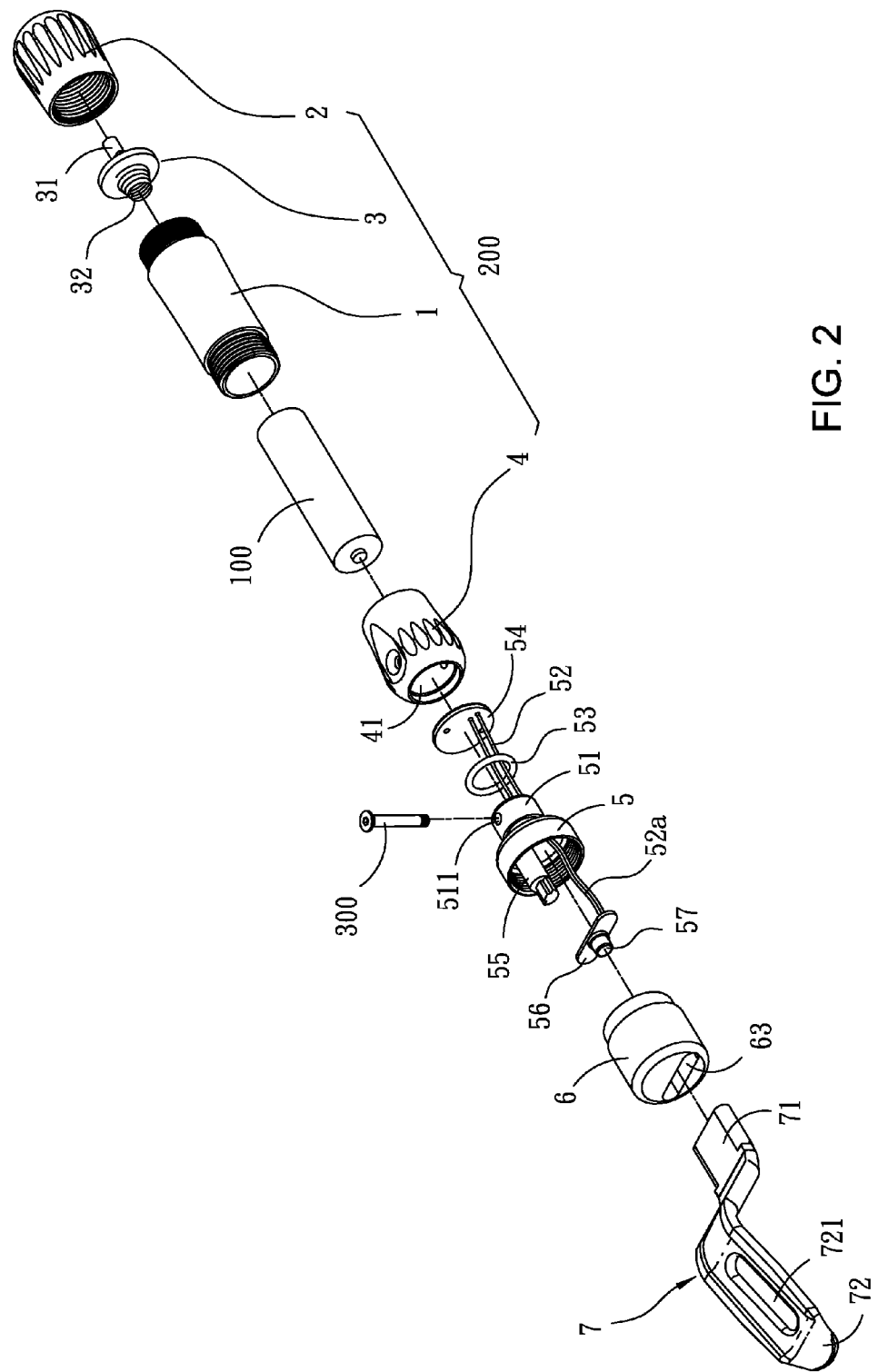
FIG. 2 corresponds to FIG. 1 when viewed from another angle.

Referring to FIGS. 1 and 2, a light guide type pain reliever in accordance with the present invention is shown. As illustrated, the light guide type pain reliever comprises a barrel 1, a battery 100 accommodated in the barrel 1, a rear end cap 2 capped on a rear end of the barrel 1, a pushbutton 21 mounted in a rear end of the rear end cap 2, and a switching connector 3. The switching connector 3 is made in the form of a circuit board and mounted in the rear end cap 2 and comprises a conducting terminal 32 made in the form of a metal spring and located at a front side thereof and stopped against the negative terminal of the battery 100 and a switching rod 31 located at a rear side thereof and connected to the pushbutton 21 and movable by the pushbutton 21 to switch on/off the battery 100. A front end cap 4 is capped on a front end of the barrel 1 and constitutes with the barrel 1 and the rear end cap 2 a handle 200 for gripping by the user and defining therein a center through hole 41. A hollow holder shell 5 has a tubular bottom neck 51 inserted into the center through hole 41. A screw bolt 300 is transversely inserted through the front end cap 4 and a transverse mounting hole 511 on the tubular bottom neck 51 to fasten the front end cap 4 and the hollow holder shell 5 together. A gasket ring 53 is mounted around the tubular bottom neck 51 and sealed in between the front end cap 4 and the tubular bottom neck 51. A plate electrode 54 is mounted in the front end cap 4 and electrically kept in contact with the positive terminal of the battery 100. A first electrical wire 52 electrically connects between the plate electrode 54 and the holder shell 5. A vibrator 55 is mounted in the holder shell 5, and a substrate 56 is accommodated in the holder shell 5. A light-emitting device 57, for example, an LED, is installed in the substrate 56. A second electrical wire 52a is electrically connected between the holder shell 5 and the substrate 56, and a selector switch 58 selects operating modes, for example, the mode of exclusively driving the light-emitting device 57 to give off light, the mode of exclusively driving the vibrator 55 to vibrate, or the mode of driving the light-emitting device 57 to give off light and the vibrator 55 to vibrate at the same time.

Figure 3:
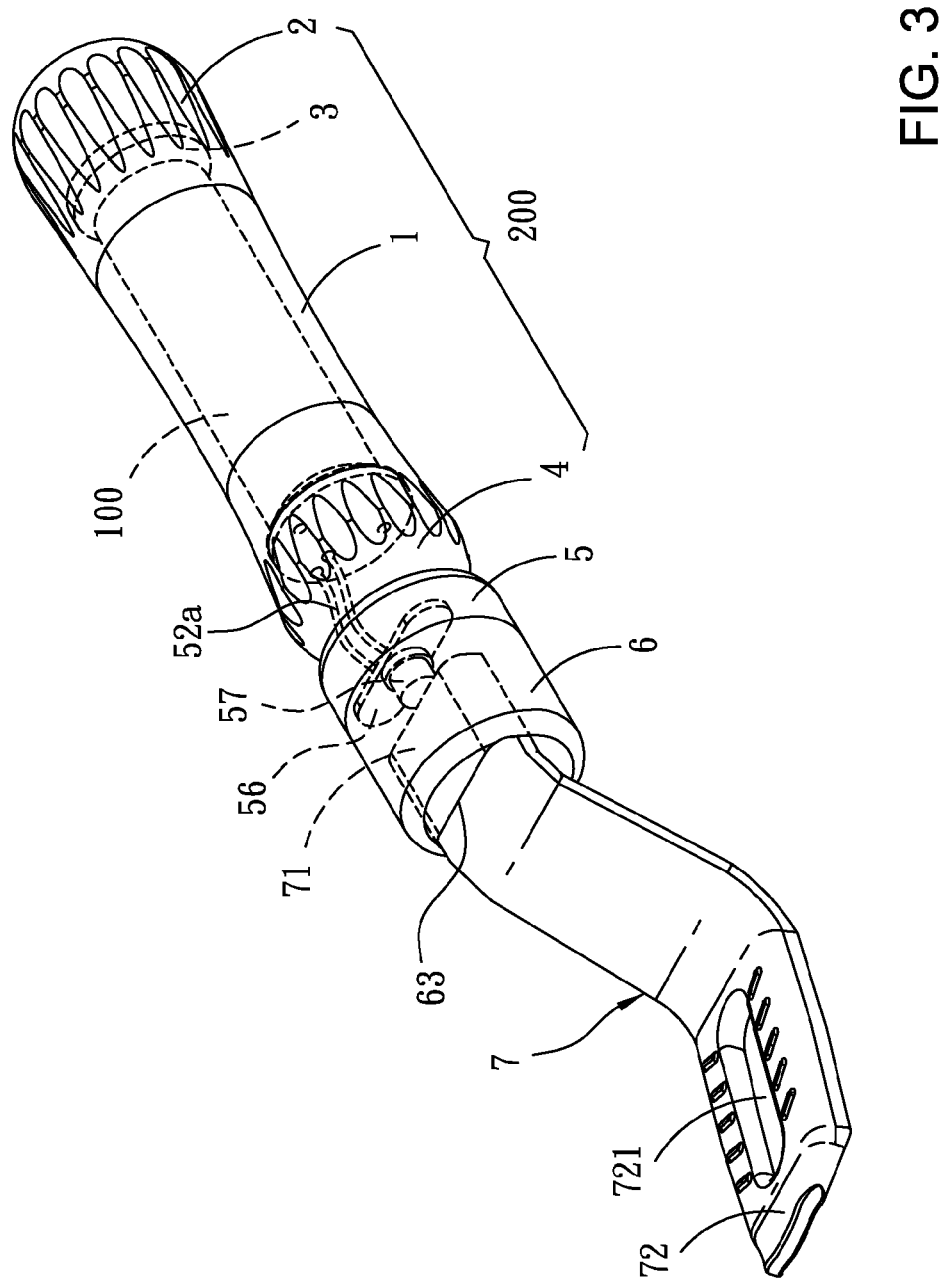
FIG. 3 is a perspective view of the light guide type pain reliever in accordance with the present invention.

Referring to FIGS. 1 and 2 again, the light guide type pain reliever further comprises an adapter 6 and a light guide plate 7 coupled to the holder shell 5 by the adapter 6. The adapter 6 comprises a locating slot 61 and a vibrator hole 62 located in the rear side thereof, and a plug hole 63 located in the front side thereof. The locating slot 61 is adapted to accommodate the light-emitting device 57 and the substrate 56, enabling the light-emitting device 57 to be kept inside the adapter 6. The vibrator hole 62 is adapted to accommodate the vibrator 55, enabling the adapter 6 to be vibrated by the vibrator 55. The plug hole 63 is kept in line with the locating slot 61, and is adapted for the mounting of the light guide plate 7. The light guide plate 7 is a curved plate member comprising a mounting portion 71 located at one end thereof and plugged into the plug hole 63 of the adapter 6 and kept in line with the light-emitting device 57, and a depressor portion 72 located at one end thereof. The depressor portion 72 is shaped like a closed loop, defining therein an insertion slot 721 for the insertion of a syringe to inject a medicine into a predetermined part of the patient's body. FIG. 3 illustrates the light guide type pain reliever assembled.

Figure 4:
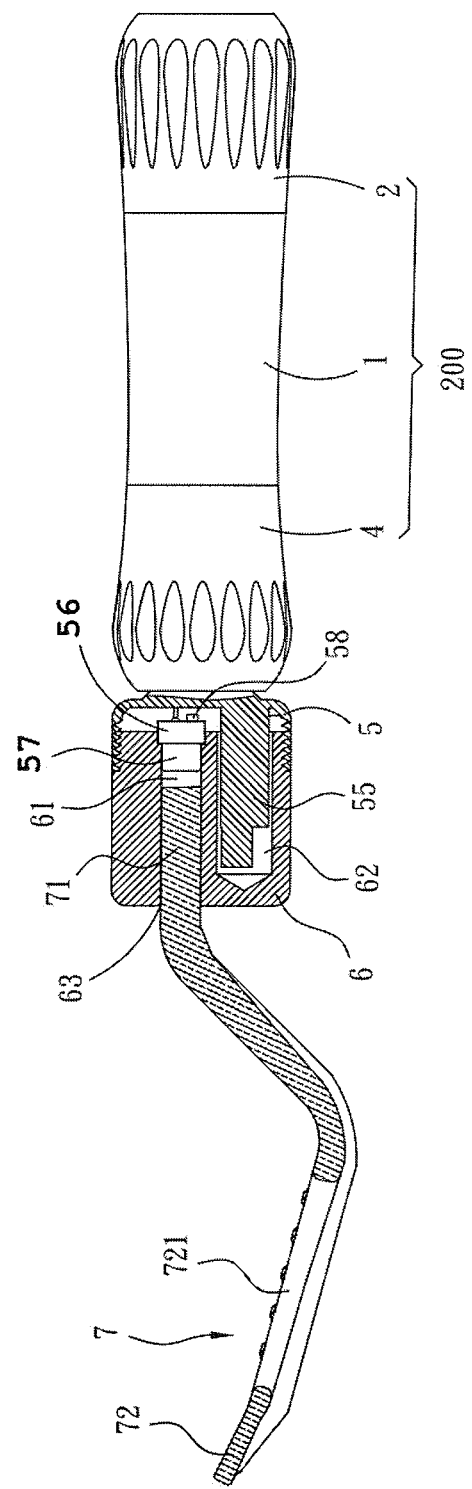
FIG. 4 is a schematic sectional view of the light guide type pain reliever in accordance with the present invention.

Referring to FIG. 4, after installation of the light guide plate 7 with the adapter 6 in the holder shell 5 at one end of the handle 200, the mounting portion 71 of the light guide plate 7 is kept in line with the light-emitting device 57. Thus, when switched on the pushbutton 21 at the rear side of the handle 200, the battery 100 is electrically conducted to the light-emitting device 57 and the vibrator 55, causing the light-emitting device 57 to give off light and the vibrator 55 to vibrate. At this time, the light guide plate 7 guides the emitted light to the depressor portion 72 for divergent illumination, enabling light rays to go in all directions around the desired area. Thus, when a physician uses the depressor portion 72 to perform an oral cavity treatment, the depressor portion 72 simultaneously illuminates the oral cavity, enabling the physician to see clearly all corners in the oral cavity. When starting the vibrator 55, the vibrator 55 will vibrate the adapter 6 and the light guide plate 7. At this time, the light guide plate 7 can be pressed on the affected area in the oral cavity of the patient to transmit vibrating waves to the affected area, and the physician can then insert the needle of the syringe through the insertion slot 721 in the depressor portion 72 into the affected area in the oral cavity of the patient to inject a medicine. Subject to the effects of vibration on the affected area, the patient will feel less pain in the affected area.

Figure 5B:
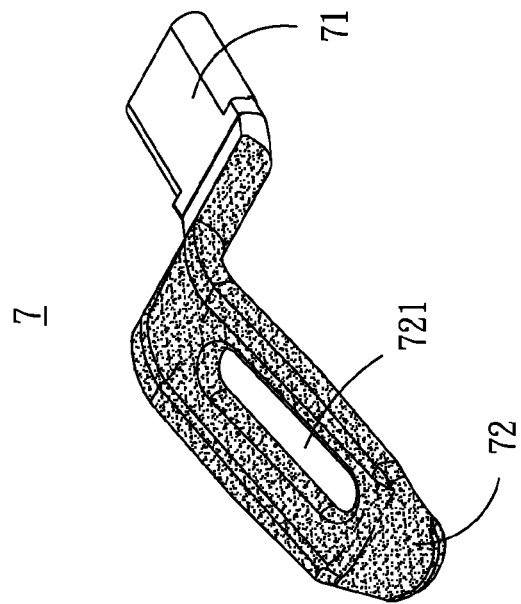
FIG. 5b is an oblique bottom elevation of the light guide plate of the light guide type pain reliever in accordance with the present invention.
Figure 5A:
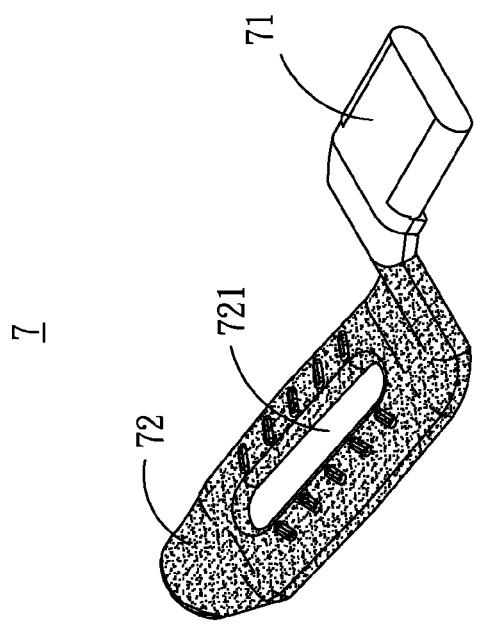
FIG. 5a is an oblique top elevation of the light guide plate of the light guide type pain reliever in accordance with the present invention.

Referring to FIGS. 5a and 5b, the light guide plate 7 comprises a frosted structure of beads or tiny rhombic facets on opposing top and bottom surfaces for reflecting incident light rays in different directions, enhancing the uniformity of illumination. Thus, the physician can selectively press the top surface or bottom surface of the light guide plate 7 on the patient's affected area, giving sufficient illumination.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A light guide type pain reliever comprising:
    a hollow handle, with said hollow handle comprising a barrel accommodating therein a battery, a rear end cap capped on one end of said barrel, a pushbutton mounted in said rear end cap, a front end cap thread-connected to an opposite end of said barrel, and a switching connector mounted in said rear end cap and electrically connected to said battery, with said switching connector comprising a switching rod linked to said pushbutton and drivable by said pushbutton to switch on/off said battery;
    a holder shell being a hollow member connected to said front end cap and electrically coupled to said battery;
    a vibrator and a light-emitting device each electrically connected to the battery;
    an adapter connected to said holder shell and including rear and front sides opposite to each other, wherein said adapter comprises a locating slot and a vibrator hole, with the locating slot extending from the rear side to a plug hole located in the front side, with the vibrator hole extending from the rear side spaced from, parallel to and not intersecting the locating slot, with said light-emitting device received in the locating slot adjacent the rear side, with said vibrator received in the vibrator hole adjacent the rear side and spaced from and parallel to the light-emitting device; and
    a light guide plate having one end thereof plugged into said plug hole of said adapter and kept in line with said light-emitting device for receiving light rays emitted by said light-emitting device and an opposite end thereof suspended outside said adapter and provided with an insertion slot, with the vibrator being coextensive to the light-emitting device and the one end of the light guide plate, and with the vibrator vibrating the adapter and the light guide plate.

2. The light guide type pain reliever as claimed in claim 1, wherein said front end cap defines a center through hole for the connection of said holder shell.

3. The light guide type pain reliever as claimed in claim 2, wherein said holder shell comprises a tubular bottom neck inserted into said center through hole of said front end cap, a mounting hole transversely located in said tubular bottom neck, and a screw bolt inserted through said mounting hole to fasten said holder shell to said front end cap.

4. The light guide type pain reliever as claimed in claim 3, further comprising a gasket ring mounted around said tubular bottom neck and sealed between said front end cap and said holder shell.

5. The light guide type pain reliever as claimed in claim 1, further comprising a plate electrode electrically connected between said battery and said holder shell.

6. The light guide type pain reliever as claimed in claim 1, further comprising a substrate electrically connected to said holder shell and carrying said light-emitting device.

7. The light guide type pain reliever as claimed in claim 6, wherein said holder shell has mounted therein a selector switch for controlling operating modes of said vibrator and said light-emitting device.

8. The light guide type pain reliever as claimed in claim 7, wherein said selector switch is installed in said substrate.

9. The light guide type pain reliever as claimed in claim 1, wherein said light guide plate comprises a mounting portion located at the one end thereof and plugged into said plug hole, and a depressor portion located at an opposite end thereof.

10. The light guide type pain reliever as claimed in claim 9, wherein said depressor portion is a closed loop.

11. The light guide type pain reliever as claimed in claim 1, wherein said light guide plate is a curved plate member.

12. The light guide type pain reliever as claimed in claim 1, wherein said light guide plate comprises a frosted structure on a surface thereof.

13. The light guide type pain reliever as claimed in claim 1, wherein the front end cap is located intermediate the front and rear sides of the adapter and the rear end cap.

* * * * *